United States Patent [19]

Pekkarinen et al.

[11] Patent Number: 4,583,975

[45] Date of Patent: Apr. 22, 1986

[54] INDIRECT PIEZOELECTRIC DROP COUNTER AND METHOD

[75] Inventors: Michael O. Pekkarinen, Lincolnshire; Ludwig Wolf, Jr., Crystal Lake; Walker Woodworth, Palatine, all of Ill.

[73] Assignee: Baxter Travenol Laboratories, Inc., Deerfield, Ill.

[21] Appl. No.: 717,487

[22] Filed: Mar. 29, 1985

Related U.S. Application Data

[63] Continuation of Ser. No. 565,068, Dec. 23, 1983, abandoned.

[51] Int. Cl.⁴ .............................................. A61M 5/16
[52] U.S. Cl. ................................... 604/253; 310/311; 128/DIG. 13
[58] Field of Search .................. 604/50, 65, 66, 67, 604/245, 251, 253; 310/311, 313 R, 334, 336, 323; 73/861.41; 128/DIG. 12, DIG. 13

[56] References Cited

U.S. PATENT DOCUMENTS

| | | |
|---|---|---|
| 3,500,366 | 3/1970 | Chesney et al. ......... 128/DIG. 13 X |
| 3,557,616 | 1/1971 | Landon, Jr. et al. . |
| 3,563,090 | 2/1971 | Deltour . |
| 3,596,515 | 8/1971 | Cramer . |
| 3,611,341 | 10/1971 | Craig et al. ..................... 310/311 X |
| 3,881,353 | 5/1975 | Fathauer . |
| 3,898,983 | 8/1975 | Elam ....................... 128/DIG. 13 X |
| 3,990,443 | 11/1976 | Fletcher ................ 128/DIG. 13 X |
| 4,018,362 | 4/1977 | Ubaud . |
| 4,037,598 | 7/1977 | Georgi . |
| 4,073,193 | 2/1978 | Mastandrea . |
| 4,105,028 | 8/1978 | Sadlier et al. ......... 128/DIG. 13 X |
| 4,131,815 | 12/1978 | Bontright ............... 310/323 |
| 4,137,940 | 2/1979 | Faisandier . |
| 4,181,130 | 1/1980 | Bailey . |
| 4,282,532 | 8/1981 | Markham . |
| 4,286,590 | 9/1981 | Murase . |
| 4,296,417 | 10/1981 | Markham et al. . |
| 4,314,484 | 2/1982 | Bowman . |
| 4,346,606 | 8/1982 | Cannon et al. . |
| 4,383,252 | 5/1983 | Purcell et al. .......... 128/DIG. 13 X |
| 4,401,909 | 8/1983 | Gorsek ............................... 310/323 |
| 4,419,598 | 12/1983 | Spitz et al. ......................... 310/311 |
| 4,419,599 | 12/1983 | Micheron ......................... 310/311 |

FOREIGN PATENT DOCUMENTS 18817 11/1980 European Pat. Off. ............ 604/253

OTHER PUBLICATIONS

"Piezoelectric Transducers", on or before 6/24/83, p. 124.
"Machine Design", on or before 4/10/83, p. 46.
"Kynar Piezofilm", on or before 4/10/83.

Primary Examiner—Edward M. Coven
Attorney, Agent, or Firm—Paul C. Flattery; Robert A. Benziger; Kay H. Pierce

[57] ABSTRACT

The present invention provides an accurate method and apparatus for monitoring the drop flow rate from a fluid source. The drops are indirectly sensed by piezoelectric means mounted on a drip chamber when the drops impinge on a fluid surface in the chamber. The chamber can include a second differential piezoelectric sensing element, which provides a noise reference signal which can be subtracted from the drop sensing signal. The volume of the fluid drops sensed can be determined. The sensing element can be incorporated in open and closed loop disposable chamber modules which can include both monitoring and occlusion valving functions integral therewith.

3 Claims, 7 Drawing Figures

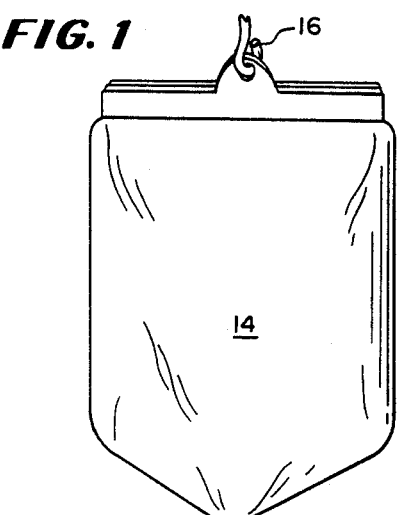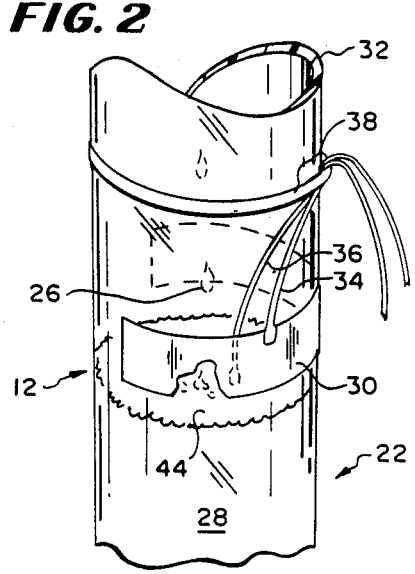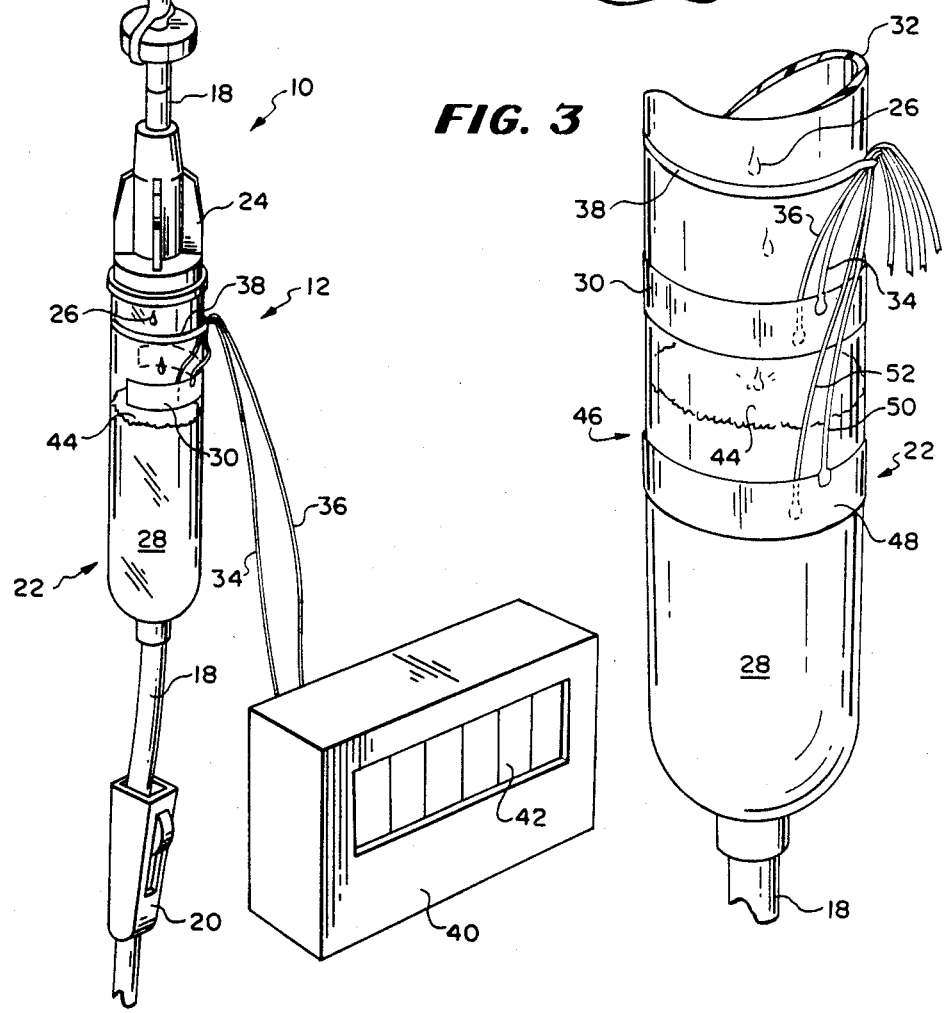

INDIRECT PIEZOELECTRIC DROP COUNTER AND METHOD

This application is a continuation of application Ser. No. 565,068, filed Dec. 23, 1983, now abandoned.

BACKGROUND OF THE INVENTION

The present invention pertains to an improved drop detection method and apparatus. More particularly, the present invention is directed to a method and apparatus for indirectly detecting fluid drops as they are collected in a drip chamber by piezoelectric means. A direct sensing method is disclosed in Ser. No. 564,997 filed concurrently herewith, entitled Direct Piezoelectric Drop Counter, assigned to the assignee herein, and incorporated herein by reference.

The invention is contemplated specifically for use in the administration of parenteral solutions to patients in hospitals and the like, but it also can be utilized for detecting and controlling drop flow of any liquid in precise quantities over a desired period of time into chemical or biological reactors, industrial processes, and the like.

While the administration of parenteral solutions is a common practice in hospitals, and great quantities of equipment of many different types are sold for the purpose of providing such administration, in many instances the medical situation calls for the administration of precisely controlled amounts of medication on a continuous drip basis over a period which may last several days or weeks. Cancer chemotherapy agents, for example, may be administered in this manner.

For these agents, and for many other medications, they must, of course, be administered to the patient in sufficient quantities to be effective, and often a uniform, continuous low volume dose is required. At the same time, an accidental increase in the flow rate can be life threatening in the case of some medications, and thus must be totally avoided.

The drop flow from conventional, gravity-operated parenteral solution equipment can vary widely, because of a range of variable situations that can occur, such as head height changes, patient blood pressure changes and changes in the controlling orifice due to tubing cold flow. These and other effects can cause intermittent or widely varying drop flow.

In the prior art, numerous patents exist which suggest various systems for controlling the flow of parenteral solution through a large assortment of electronic devices which purportedly provide improved flow accuracy. As a typical example of such prior art, drops of the solution are formed and fall through a conventional drip chamber in an administration set and are detected as they fall by a drop detector which can operate on photometric principles, by sensing variations in capacitance, or the like. A flow control clamp valve or other occlusion device is provided in the flow conduit and is controlled by a feedback mechanism, typically electronic, for sensing the drop rate in the drip chamber and appropriately controlling the valve so that the drop rate is kept within desired parameters.

In the prior art, a pump often is used to propel the solution through the set. This carries its own hierarchy of risks, and requires the presence of safety systems to prevent the pumping of air into the patient in the event that the source of parenteral solution runs dry. Such safety systems are, of course, subject to breakdown and failure, and the consequences of that also potentially are fatal.

It therefore is preferable, for safety and simplicity, to utilize a gravity operated system which measures amounts of parenteral solution to a patient. The utilization of the prior photometric drop detectors can cause numerous problems. The photometric or electro-optic detectors generally are relatively expensive, are easily misaligned, are easily damaged, such as by falling off the drip chamber, have large power requirements and otherwise can cause a variety of operational problems. The prior detectors also do not determine the volume of the fluid drops sensed.

SUMMARY OF THE INVENTION

In accordance with the present invention, a method and apparatus is provided to precisely monitor the drop flow rate from a fluid source. The invention provides for the indirect sensing of drops collected in a drip chamber by piezoelectric means coupled to the drip chamber. The piezoelectric means can be mounted to the outside of the drip chamber to sense the impingement of drops therein. The invention also includes a differential sensing method and apparatus to increase the sensitivity and reliability of the drop sensor and to remove artifacts caused by environmental "noise," such as vibrations, temperature changes, etc. The volume of the fluid drops which are sensed can also be determined. Also incorporated in the invention are a number of disposable product application modules.

BRIEF DESCRIPTION OF THE DRAWINGS

FIG. 1 is a perspective view of a drop detecting system incorporating the invention;

FIG. 2 is an enlarged partial perspective view of the sensing portion of FIG. 1;

FIG. 3 is an enlarged partial perspective view of the sensing portion of a differential embodiment of the invention.

DETAILED DESCRIPTION OF THE PREFERRED EMBODIMENTS

Figure 4A:
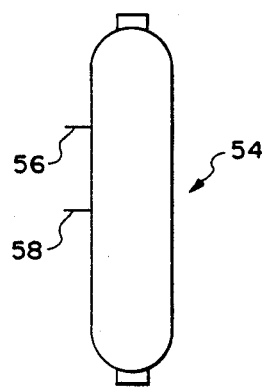
FIGS. 4A–4D are diagrammatic modular product application embodiments of the invention.

Referring to FIG. 1, a drop detecting system 10 is illustrated which incorporates a first embodiment of a drop sensor or detector 12 of the invention. A fluid to be detected and administered, such as a parenteral solution, is contained in a fluid source or container 14. The source 14 is generally mounted onto a hook 16, which is part of a mobile administration unit (not illustrated).

The fluid source can be part of a parenteral solution set which includes a flexible collapsible tubing 18, through which the fluid passes to a patient or other communication set. The set can include a clamp 20 to close off the fluid flow when desired. The fluid passes through a drip chamber 22, which includes the drop sensor 12.

The fluid passes first into a drop forming portion 24 of the chamber 22. The drop former 24 can be of any conventional type and generally is designed to form 10 drops per cubic centimeter of fluid (called regular drops hereinafter) or 60 drops per cubic centimeter of fluid (called mini drops hereinafter). The drops 26 fall into a drop collecting portion 28 of the chamber 22.

Referring to FIGS. 1 and 2, the sensor 12 includes at least one piezoelectric element 30. The element 30 preferably is a polymeric piezoelectric film, such as a vinylidene fluoride based film sold under the name "Kynar" by Pennwalt Corporation. These films are pliant, flexible, tough, lightweight and very inexpensive compared to the optical drop sensing systems presently being utilized.

The element 30 can be mounted on a portion of a wall 32 of the chamber 22 by any conventional technique, such as by an adhesive. The element 30 includes a pair of leads 34 and 36 which are coupled to opposite sides of the element 30. The leads 34 and 36 conveniently may be secured to the chamber 22 by a band or strap 38 and can be coupled to a monitor or counter/controller 40 or to a fluid supply pump for the container 14. The monitor 40 can include a display 42, which will display the number of drops sensed by the sensor 12 and can include a conventional alarm for counts which are out of a predetermined range.

In operation, as the drops 26 impinge on a surface 44 of accumulated fluid, the element 30 is stressed which generates a voltage difference on the leads 34 and 36, which then can be counted or monitored by the monitor 40. The magnitude of the voltage generated in response to a drop is proportional to the drop size and hence can be utilized to determine the volume of fluid sensed. The counting of the mini drops or other drops can be impeded in an environment which produces extraneous noise or vibrations, which are coupled to the chamber 22, such as by moving or hitting the hook 16 or the chamber 22.

To enhance the sensitivity and reliability of the invention, a sensor 46 is illustrated in FIG. 3, which includes a differential sensing element 48. The element 48 also is a portion of piezoelectric film which is affixed to the chamber wall 32. The element 48 includes a pair of leads 50 and 52, which also can be coupled to the monitor 40 (not illustrated). The leads 50 and 52 also can be secured by the strap 38.

The element 48 will sense any extraneous noise, vibration or temperature change to which the chamber 22 is subjected, which also affects the signal generated by the element 30. The element 48 is located far enough away from the surface 44 of the fluid, such that a substantially insignificant signal is generated by the drops 26.

The noise or reference signal generated by the element 48 can then be subtracted from the signal generated by the element 30, to substantially eliminate outside interference and increase the sensitivity and reliability of the sensor 12.

FIGS. 4A-4D illustrate product application modules which are incorporated by the invention. FIG. 4A illustrates a disposable drip chamber module 54. The module 54 includes a pair of leads 56 and 58, in the form of pins mounted on the drip chamber. The pins 56 and 58 are connected to the piezoelectric sensing element (not illustrated). The chamber module 54 can include four leads in a differential embodiment if desired.

In the embodiment of FIG. 4A, the pins 56 and 58 can be coupled to monitor leads, such as the leads 34 and 36, and all the electronics are separately included in the monitor, such as the monitor 40. Also, although not disclosed specifically, the monitor generally will also be coupled to or include an occlusion mechanism. The occlusion mechanism includes a clamp member or valve which is adjusted in response to the drop rate sensed by the detector 12.

Figure 4B:
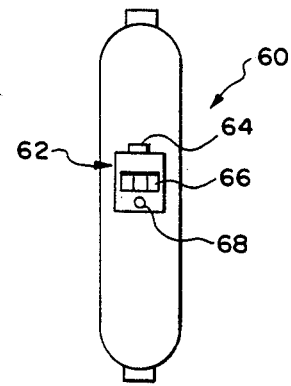

A second disposable drip chamber module 60 is illustrated in FIG. 4B. In this embodiment, a monitor 62 is mounted on the chamber 60 which forms an open loop system. Open loop is meant to be a monitoring system which does not include an occlusion or valving mechanism. The monitor 62 can be an integrated circuit module, similar in size to those presently utilized in watches and clocks, and can include a start/clear button 64, a display 66 and an alarm 68. The monitor 62 can have preset alarm limits or also can include an alarm limit set button. The monitor 62 also can include a pair of output leads (not illustrated) which can be coupled to an occlusion mechanism to form a closed loop system.

Figure 4C:
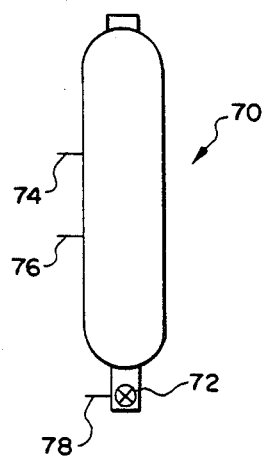

FIG. 4C illustrates another disposable drip chamber module 70, which includes an occlusion valving means 72. The chamber module 70 is a closed loop system when coupled to a monitor as described with respect to the module 54. The module 70 includes a pair of sensor output pins 74 and 76 which are coupled to the module. The valve means 72 also includes a control pin or pins 78 which is also coupled to the monitor. The output of the sensor on the pins 74 and 76 is utilized by the monitor to control the valve means 72 through the pin 78.

Figure 4D:
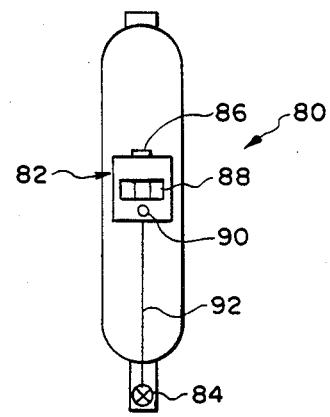

An integrated closed loop disposable module 80 is illustrated in FIG. 4D. The module 80 includes a monitor 82, which can again be an integrated circuit, and valve means 84. The monitor 82 also can include a start/clear button 86, a display 88 and an alarm 90. The monitor also includes the occlusion electronics to control the valve means 84 on a control line or lines 92. Thus, the module 80 includes a fully operable drop sensing and occlusion mechanism which is a fraction of the cost of the present optical sensing systems and is fully disposable.

Modifications and variations of the present invention are possible in light of the above teachings. The sizes and types of the piezoelectric elements can be selected as desired for the intended application. The elements can be single elements or can be an array of the elements and the elements can be formed on the drip chamber modules as a portion thereof. The disposable modules also preferably include a drop former therein, but can also be provided with an external drop former. The single sensing element can be below the fluid level, but a location above the level is preferred. It is therefore to be understood that within the scope of the appended claims the invention may be practiced otherwise than as specifically described.

What is claimed and desired to be secured by Letters Patent of the United States is:

1. A method of detecting fluid drops from a fluid source, comprising:
   directing drops of fluid onto a surface of accumulated fluid in a drip chamber;
   providing a first piezoelectric film means coupled to said drip chamber for sensing and generating a signal as each drop impinges on said surface;
   providing second differential piezoelectric film means coupled to said chamber and spaced from said first piezoelectric film means to generate reference signals proportional to noise, vibration or temperature changes to which the chamber is subjected.

2. An apparatus for detecting fluid drops from a fluid source, comprising:
   drip chamber means for accumulating fluid;
   means for directing drops of fluid onto an upper surface of the accumulated fluid in said chamber means;

first piezoelectric film means affixed to said chamber means for sensing the impingement of each drop on said surfaces and for generating a signal for each sensed drop wherein said first piezoelectric film means includes a flexible piezoelectric film mounted on the outside of said chamber means above said fluid surface; and second differential piezoelectric film means affixed to said chamber means and spaced from said first piezoelectric means to generate reference signals produced by stresses on said chamber means with said second film means positioned below said fluid surface.

3. The apparatus as defined in claim 2 wherein:

said differential piezoelectric film means includes a second flexible piezoelectric film mounted on the outside of the said chamber means below fluid surface.

* * * * *